United States Patent
Kapre et al.

(10) Patent No.: US 9,198,977 B2
(45) Date of Patent: Dec. 1, 2015

(54) IMMUNOGENIC COMPOSITION

(71) Applicant: Serum Institute of India Ltd., Pune (IN)

(72) Inventors: Subhash Vinayak Kapre, Pune (IN);
Sambhaji Shankar Pisal, Pune (IN)

(73) Assignee: Serum Institute of India Ltd., Pune (IN)

( * ) Notice: Subject to any disclaimer, the term of this patent is extended or adjusted under 35 U.S.C. 154(b) by 0 days.

(21) Appl. No.: 14/375,385

(22) PCT Filed: Jan. 29, 2013

(86) PCT No.: PCT/IB2013/050739
§ 371 (c)(1),
(2) Date: Jul. 29, 2014

(87) PCT Pub. No.: WO2013/114268
PCT Pub. Date: Aug. 8, 2013

(65) Prior Publication Data
US 2014/0377302 A1    Dec. 25, 2014

(30) Foreign Application Priority Data
Jan. 30, 2012  (IN) .......................... 281/MUM/2012

(51) Int. Cl.
| | | |
|---|---|---|
| A61K 39/00 | (2006.01) | |
| A61K 39/02 | (2006.01) | |
| A61K 39/095 | (2006.01) | |
| A61K 39/385 | (2006.01) | |
| A61K 47/48 | (2006.01) | |

(52) U.S. Cl.
CPC ............ *A61K 47/4833* (2013.01); *A61K 39/095* (2013.01); *A61K 2039/6037* (2013.01); *A61K 2039/627* (2013.01); *A61K 2039/70* (2013.01)

(58) Field of Classification Search
CPC ................................................ A61K 47/4833
See application file for complete search history.

(56) References Cited

FOREIGN PATENT DOCUMENTS
WO    WO 2008/102173    *  8/2008

OTHER PUBLICATIONS

Mothershed et al (Journal of Clinical Microbiology vol. 42, No. 1, pp. 320-328, 2004).*
Chilukuri, Srinivas Reddy, et al., "Process development and immunogenicity studies on a serogroup 'X' Meningococcal polysaccharide conjugate vaccine," Biologicals 42 (2014) 160-168.
Drug insert for 284 Menactra vaccine for meningococcal disease (Sanofi Pasteur, vol. 11, p. 1-36, Nov. 30, 2011).
Drug insert for Menveo for meningococcal disease (p. 1-16, Mar. 2011).
LaForce, F. Marc, et al., "Epidemic meningococcal meningitis in Africa: success using a Group A conjugate vaccine and a development update on a new pentavalent ACYWX conjugate vaccine" (WHO report on conjugate vaccines, p. 1-32, Oct. 13, 2014).
World Health Organization, "Meningococcal vaccines: WHO position paper, Nov. 2011," Weekly epidemiological record 86 (2011): 521-540.
Xie, Ouli, et al., "Emergence of serogroup X meningococcal disease in Africa: Need for a vaccine." Vaccine 31 (2013) 2852-2861.

* cited by examiner

*Primary Examiner* — Albert Navarro
(74) *Attorney, Agent, or Firm* — Knobbe, Martens, Olson & Bear, LLP

(57) ABSTRACT

The invention provides immunogenic polysaccharide protein conjugates comprising capsular polysaccharides from *N. Meningitidis* serogroup X and methods for preparation thereof. The present invention relates to *N. meningitidis* X saccharide-carrier protein conjugates prepared by a conjugation reaction. Accordingly, the instant invention relates to multivalent meningococcal polysaccharide protein conjugate composition comprising capsular saccharide from serogroups X and at least one capsular saccharide from A, C, W135 and Y wherein, i) polysaccharides A C W135 X are sized mechanically whereas polysaccharide Y is sized chemically, ii) all saccharide are conjugated to carrier protein via a linker with a cyanylation conjugation chemistry iii) all saccharide to protein ratios in final conjugates are between 0.2-0.6 and iv) at least two different carrier proteins selected from the group consisting of TT, DT and CRM197 are utilized.

27 Claims, 11 Drawing Sheets

IMMUNOGENIC COMPOSITION

CROSS REFERENCE TO RELATED APPLICATIONS

This application is a U.S. National Phase Application of PCT International Application Number PCT/IB2013/050739, filed on Jan. 29, 2013, designating the United States of America and published in the English language, which is an International Application of and claims the benefit of priority to Indian Patent Application No. 281/MUM/2012, filed on Jan. 30, 2012. The disclosures of the above-referenced applications are hereby expressly incorporated by reference in their entireties.

BACKGROUND OF THE INVENTION

Neisseria meningitidis (meningococcus) is a Gram negative human pathogen. It colonizes the pharynx, causing meningitis and, occasionally, septicemia in the absence of meningitis. It is closely related to N. gonorrhoeae, although one feature that clearly differentiates meningococcus is the presence of a polysaccharide capsule that is present in all pathogenic meningococci. Based on the organism's capsular polysaccharide, twelve serogroups of N. meningitidis have been identified (A, B, C, H, I, K, L, 29E, W135, X, Y and Z).

Serogroup A ('MenA') is most common cause of epidemic disease in sub-Saharan Africa. Serogroups B & C are responsible for the majority of cases in developed countries, with the remaining cases being caused by serogroups W135 & Y.

The vaccine utilizing the polysaccharide (PS) alone have relatively low immunogenicity. To overcome the relatively low immunogenicity of polysaccharide, PS vaccines are conjugated to protein carriers to increase immunogenicity and provide long-term protection in young children. Many meningococcal conjugate vaccines are already approved and marketed throughout the world. Examples of such vaccines, known as "Neisseria meningitidis conjugates" are monovalent meningococcal A conjugate (MenAfriVac), monovalent meningococcal C conjugate (Meningitec) and quadrivalent A C Y W meningococcal conjugates (Menveo & Menactra).

As well as being used for classification, the capsular polysaccharide has been used for vaccination. An injectable tetravalent vaccine of capsular polysaccharides from serogroups A, C, Y & W135 has been known for many years and is licensed for human use. Although effective in adolescents and adults, it induces a poor immune response and short duration of protection and cannot be used in infants. Mencevax ACWY™ and Menomune™ both contain 50 μg of each purified polysaccharide once reconstituted from their lyophilised forms. The capsular saccharides of serogroups A, C, W135 & Y have also been combined in the form of conjugates to give tetravalent vaccines e.g. the unadjuvanted Menactra™ product. Also conjugated serogroup A polysaccharide have been approved for human use as MenAfriVac™, serogroup C oligosaccharides have been approved for human use as Menjugate™, Meningitec™ and NeisVac-C™.

N. meningitidis serogroup X strains were first described in the 1960s and have been isolated from a few cases of invasive meningococcal diseases in North America, Europe, Australia, and China. Outbreaks of N. meningitidis serogroup X strains have been reported in Niger, western Kenya, and northern Ghana. N. meningitidis serogroup X strains were reported to be very efficient in colonization among military recruits in the United Kingdom. Refer Abdullah Kilic et al; Neisseria meningitidis Serogroup X Sequence Type 767 in Turkey; Journal Of Clinical Microbiology, November 2010, p. 4340-4341; Vol. 48, No. 11

It was reported that repeated mass vaccination in many African countries might have contributed to colonization by and meningococcal diseases due to serogroup X strains and might result in a changed profile of meningococcal disease Refer Gagneux, S. P et al; Prospective study of a serogroup X Neisseria meningitidis outbreak in northern Ghana. J. Infect. Dis. 185:618-626; 2002.

The capsular polysaccharides of serogroup B, C, Y, and W135 meningococci are composed of sialic acid derivatives. Serogroup B and C meningococci express ($\alpha$ 2-8)- and ($\alpha$2-9 239)-linked polysialic acid, respectively, while alternating sequences of D-glucose or D-galactose and sialic acid are expressed by serogroup Y and W135 N. meningitidis. In contrast, the capsule of serogroup A meningococci is composed of ($\alpha$ 1-6)-linked N-acetylmannosamine 6-phosphate, while N. meningitidis serogroup X synthesizes capsular polymers of ($\alpha$ 1-4)-linked N-acetylglucosamine 1-phosphate. Refer Yih-Ling Tzeng et al; Genetic Basis for Biosynthesis of the (134)-Linked N-Acetyl-D-Glucosamine 1-Phosphate Capsule of Neisseria meningitidis Serogroup X; Infection And Immunity, December 2003, p. 6712-6720; Vol. 71, No. 12

The existing meningococcal conjugate vaccines are based on A C Y W135 polysaccharides. The increase in incidence of MenX disease in African Meningitis Belt in the last 5 years [1,4] warrants development and introduction of a MenX polysaccharide conjugate vaccine in selected areas of the region to prevent and control future epidemics. Though has been reported earlier. In spite of availability of comprehensive seroprevalence and structural data for meningococcal X, a commercially viable conjugate vaccine including X polysaccharide is yet to be developed due to extremely limited success on purification, conjugation and formulation stability aspects for the same. This provides an additional challenge for successfully addressing and controlling various parameters, especially when employing a scalable conjugation process for the large-scale manufacture of Neisseria meningitidis conjugates containing Neisseria meningitidis X polysaccharide.

The present invention arises from the surprising discovery that it is possible to prepare a monovalent or multivalent immunogenic composition based on conjugates of meningococcal polysaccharide from serogroup X by utilizing a scalable and efficient conjugation process.

SUMMARY OF THE INVENTION

The present invention relates to N. meningitidis X saccharide-carrier protein conjugates prepared by a conjugation reaction comprising of i) sizing of polysaccharide ii) CPPT based activation of sized polysaccharide having average molecular weight between 100-150 Kda, at a pH between 9 to 9.5 iii) ADH addition after a duration of about 2 to 5 minutes followed by incubation period of 4-20 hrs and iv) reacting ADH activated polysaccharide with purified non-activated carrier protein in a ratio between 0.75-1.5 in presence of MES buffer and EDAC followed by incubation period of 3-4 hrs, characterized in that the conjugation reaction is carried at 2-8° C. resulting in a conjugate yield from 20% to about 30% and having saccharide to protein ratio from 0.2 to about 0.6 in final conjugate.

Alternatively, N. meningitidis X saccharide-carrier protein conjugates can also be prepared by a conjugation reaction comprising of i) sizing of polysaccharide ii) CPPT based activation of sized polysaccharide having average molecular weight between 100-150 Kda, at a pH between 9 to 9.5 iii) addition of ADH activated carrier protein in a saccharide:protein ratio between 0.5-2 after 2-3 minutes followed by incubation period of 2 to 20 hrs characterized in that the conjugation reaction is carried at 22° C. to 25° C. resulting in a conjugate yield from 5% to about 10%.

Accordingly, the instant invention relates to multivalent meningococcal polysaccharide protein conjugate composition comprising capsular saccharide from serogroups X and at least one capsular saccharide from A, C, W135 and Y wherein, i) polysaccharides A C W135 X are sized mechanically whereas polysaccharide Y is sized chemically, ii) all saccharide are conjugated to carrier protein via a linker with a cyanylation conjugation chemistry iii) all saccharide to protein ratios in final conjugates are between 0.2-0.6 and iv) at least two different carrier proteins selected from the group consisting of TT, DT and CRM197 are utilized.

DETAILED DESCRIPTION OF THE INVENTION

Figure 1:
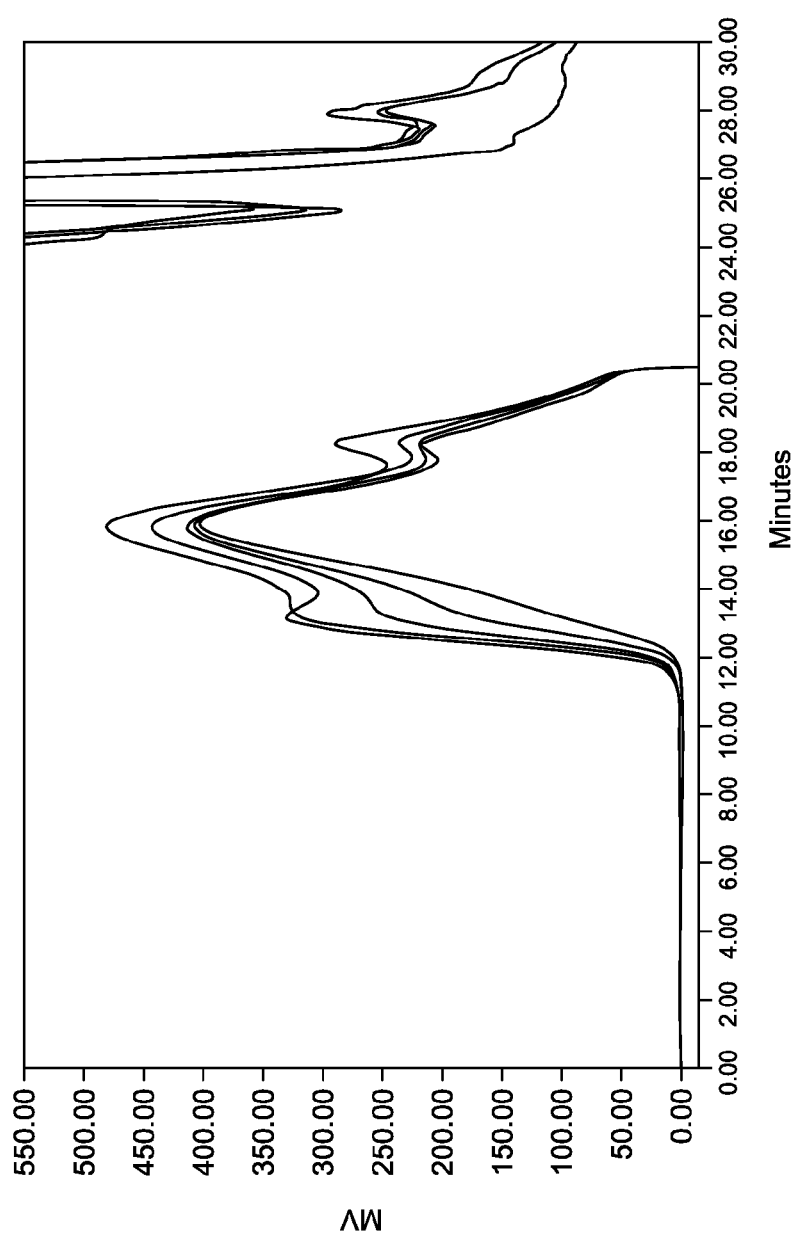
FIG. 1: Overlay of conjugation reaction when Men X Ps (215 KDa) conjugated to Hydrazine derivatized TT
Figure 2:
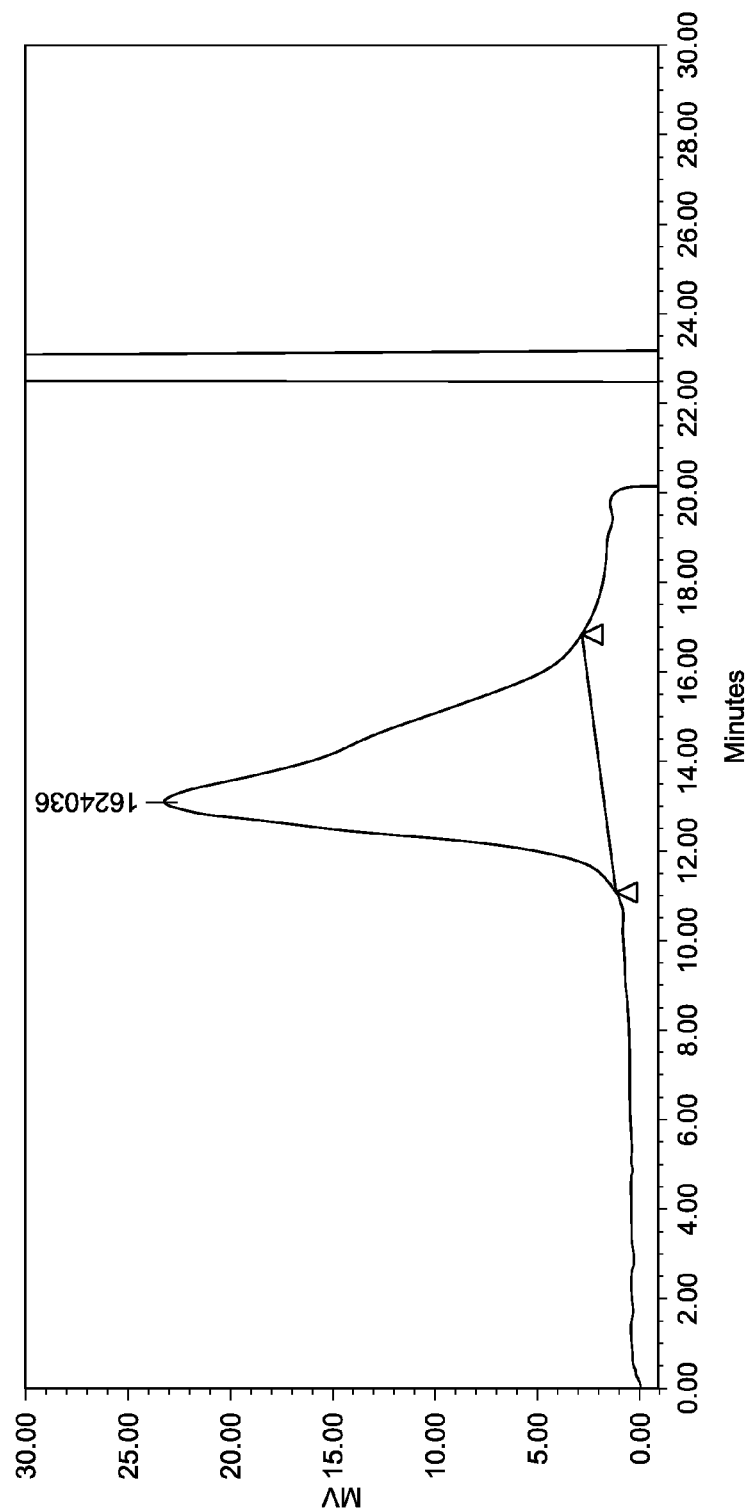
FIG. 2: Purified Conjugate when Men X Ps (215 KDa) conjugated to Hydrazine derivatized TT
Figure 3:
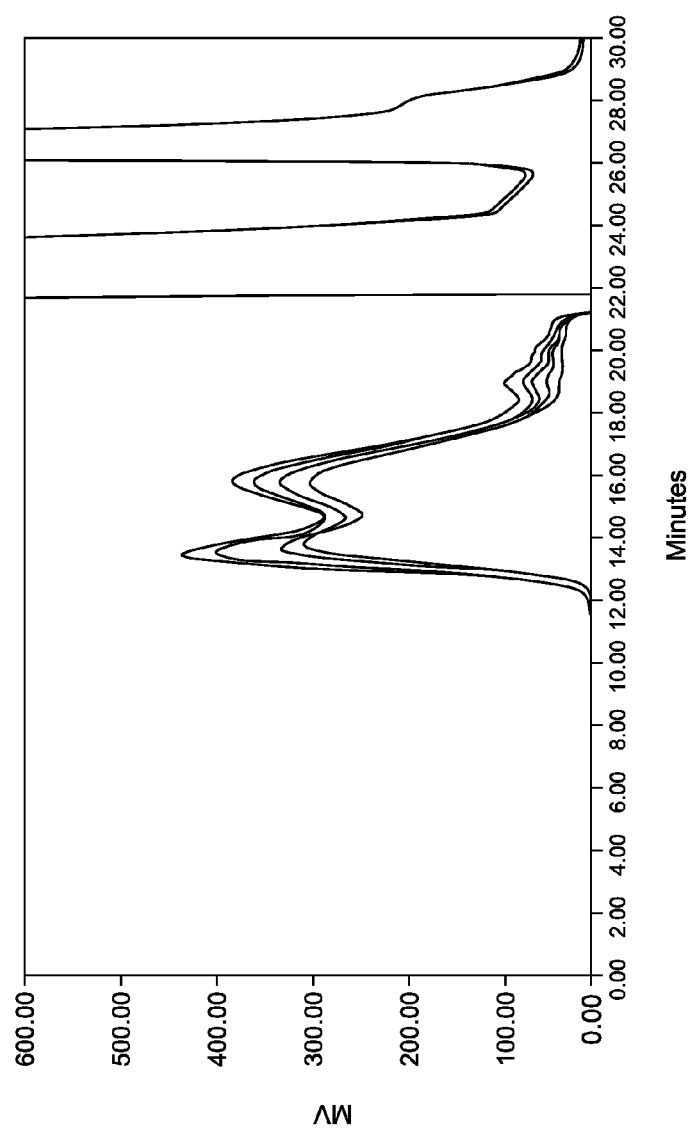
FIG. 3: Overlay of conjugation reaction when Men X Ps (326 KDa) conjugated to ADH derivatized TT
Figure 4:
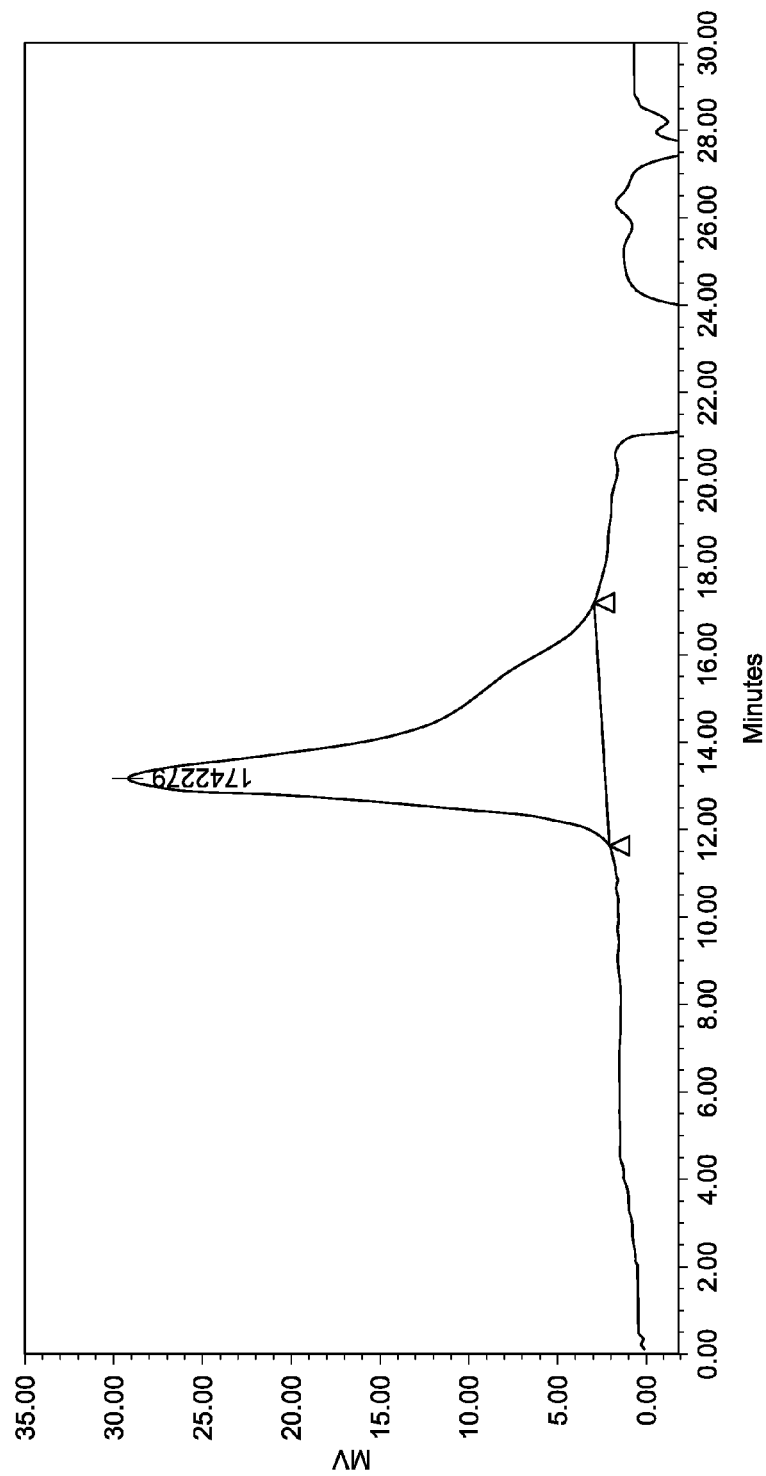
FIG. 4: Purified Conjugate when Men X Ps (326 KDa) conjugated to ADH derivatized TT
Figure 5:
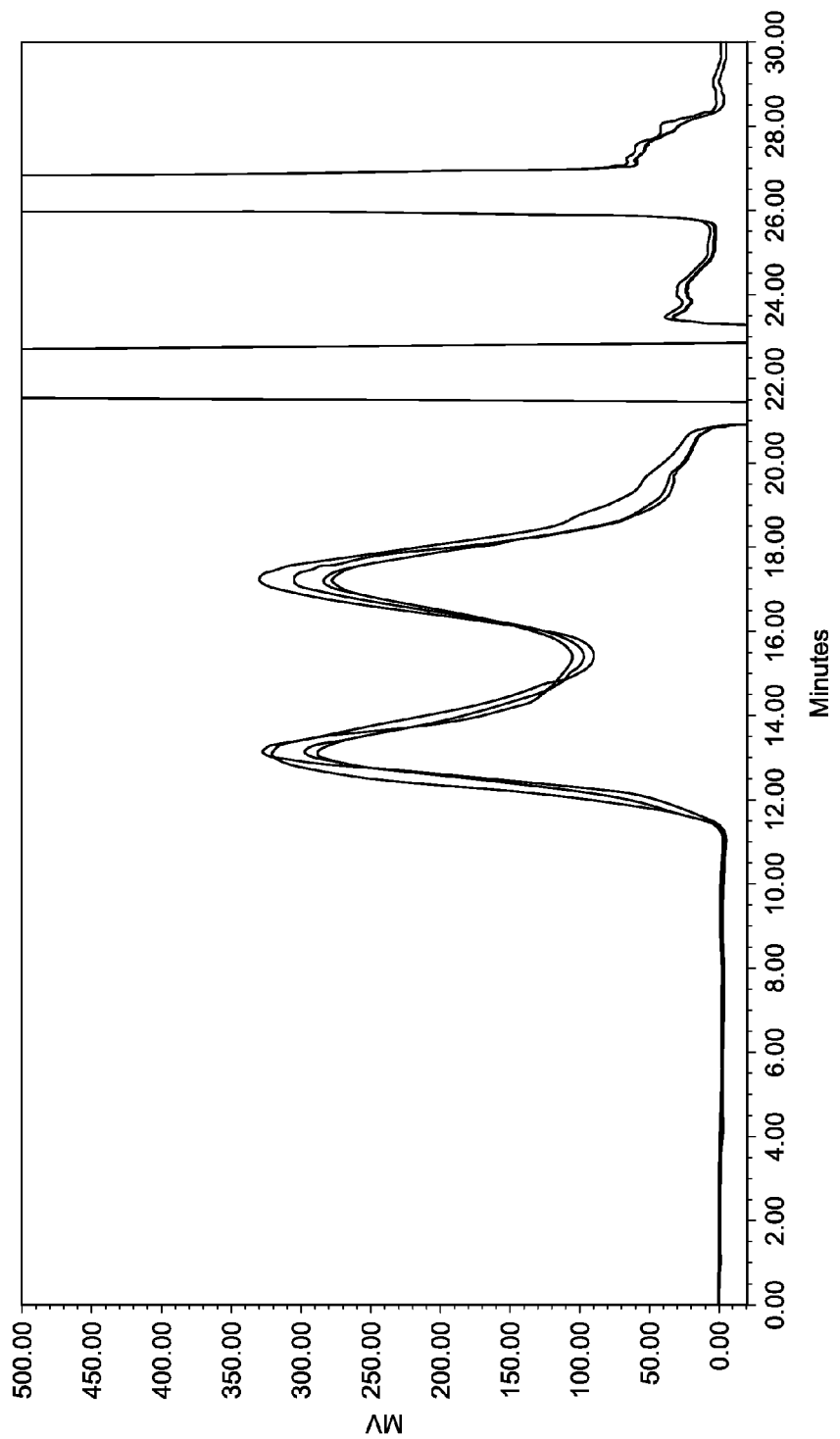
FIG. 5: Overlay of conjugation reaction when Men X Ps (120 KDa) conjugated to ADH derivatized TT
Figure 6:
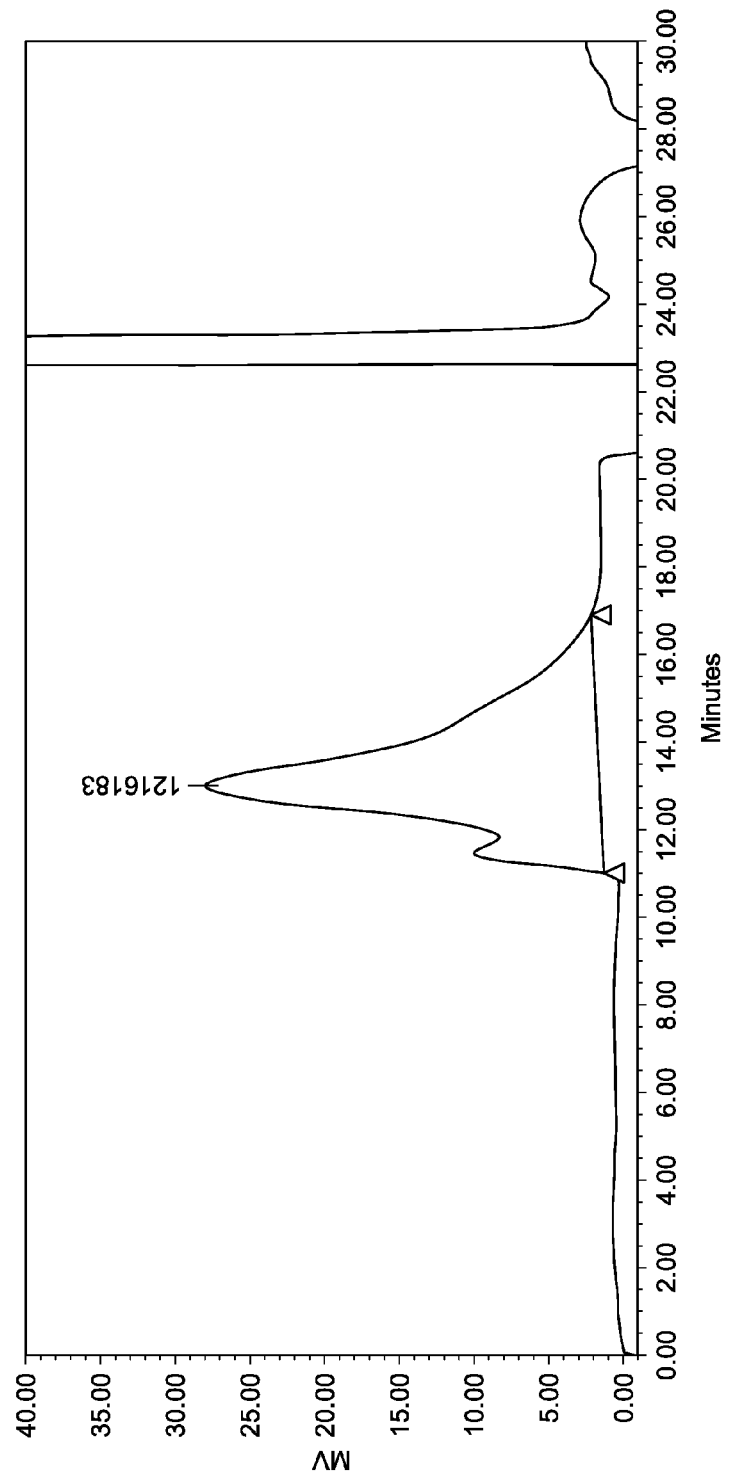
FIG. 6: Purified Conjugate when Men X Ps (120 KDa) conjugated to ADH derivatized TT
Figure 7:
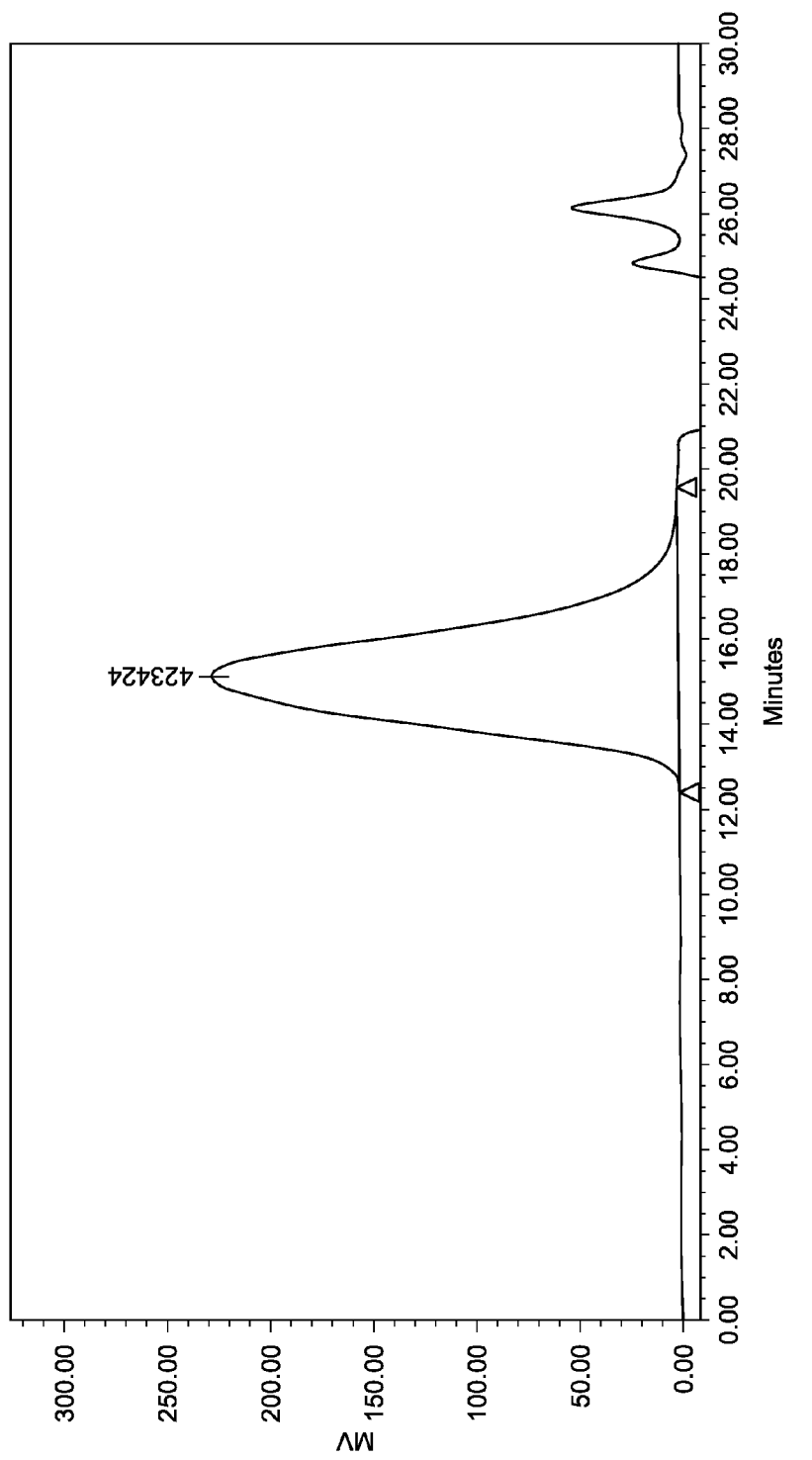
FIG. 7: Chromatogram of Native Meningococcal X polysaccharide.
Figure 8:
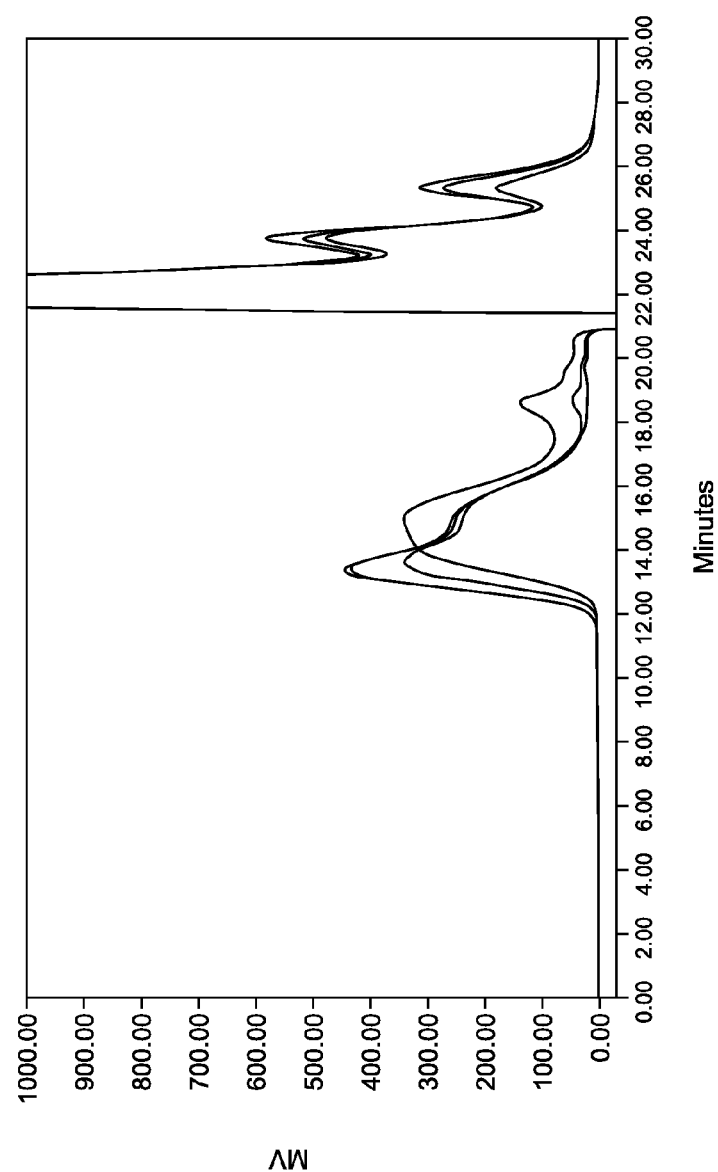
FIG. 8: Overlay of conjugation reaction when Men X Ps (510 KDa) activated with ADH and conjugated to purified TT.
Figure 9:
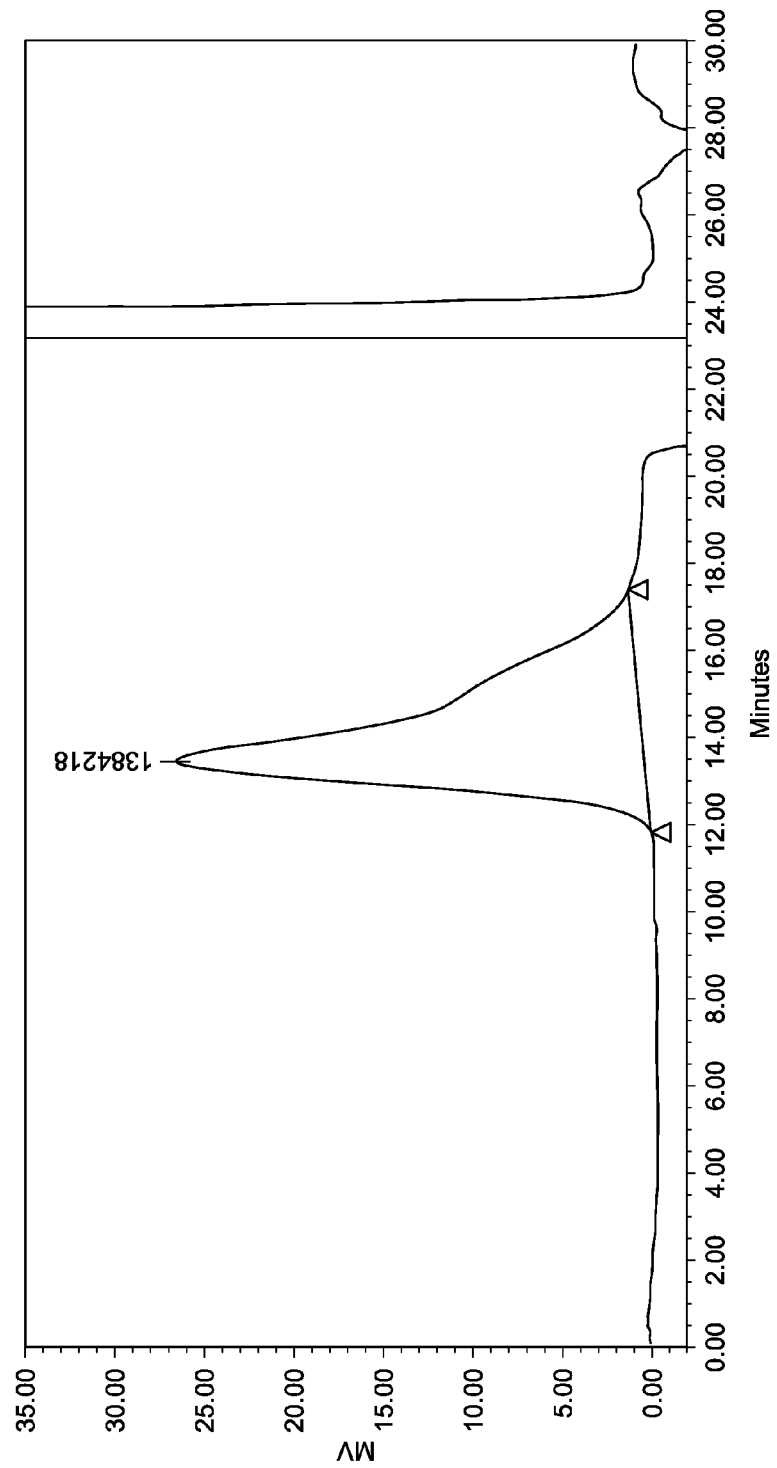
FIG. 9: Purified Conjugate when Men X Ps (510 KDa) activated with ADH and conjugated to purified TT.
Figure 10:
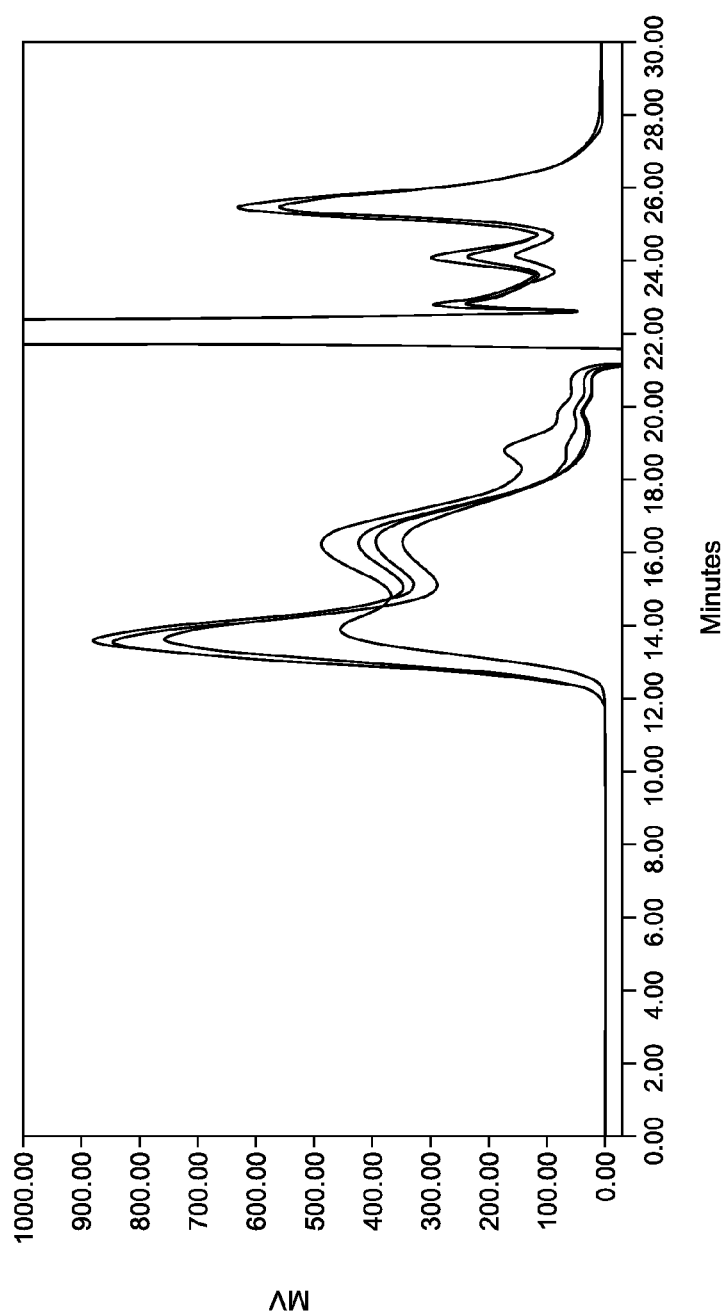
FIG. 10: Overlay of conjugation reaction when Men X Ps (250 KDa) activated with ADH and conjugated to purified TT.
Figure 11:
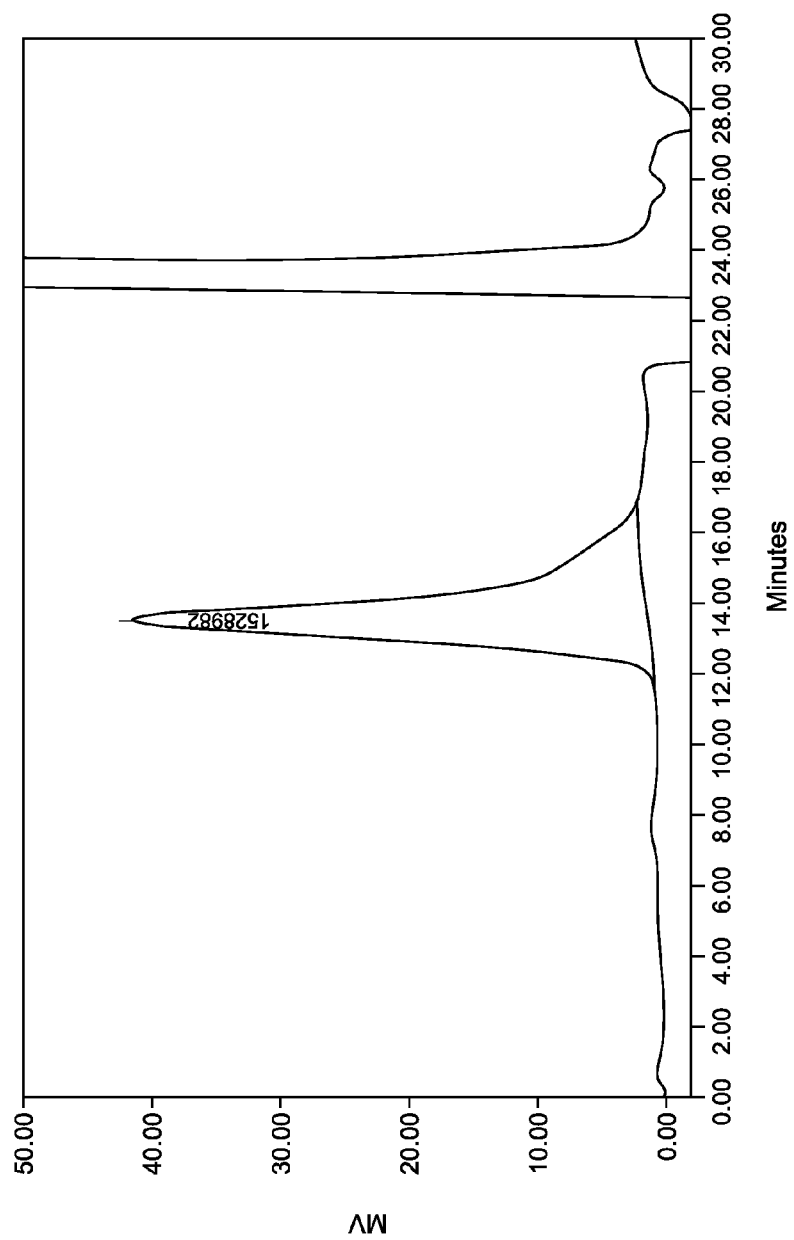
FIG. 11: Purified Conjugate when Men X Ps (250 KDa) activated with ADH and conjugated to purified TT.

"Multivalent immunogenic compositions" refer to:

Composition I comprises (a) a conjugate of (i) the capsular saccharide of serogroup A *N meningitidis* and (ii) tetanus toxoid; (b) a conjugate of (i) capsular saccharide of serogroup C *N meningitidis* and (ii) tetanus toxoid; (c) a conjugate of (i) capsular saccharide of serogroup Y *N. meningitidis* and (ii) diphtheria toxoid; (d) a conjugate of (i) capsular saccharide of serogroup W135 *N. meningitidis* and (ii) tetanus toxoid; and (d) a conjugate of (i) capsular saccharide of serogroup X *N meningitidis* and (ii) tetanus toxoid.

Composition II comprises (a) a conjugate of (i) the capsular saccharide of serogroup A *N meningitidis* and (ii) tetanus toxoid; (b) a conjugate of (i) capsular saccharide of serogroup C *N meningitidis* and (ii) CRM197; (c) a conjugate of (i) capsular saccharide of serogroup Y *N. meningitidis* and (ii) tetanus toxoid; (d) a conjugate of (i) capsular saccharide of serogroup W135 *N. meningitidis* and (ii) CRM197; and (d) a conjugate of (i) capsular saccharide of serogroup X *N meningitidis* and (ii) CRM197.

Composition III comprises (a) a conjugate of (i) the capsular saccharide of serogroup A *N meningitidis* and (ii) CRM 197; (b) a conjugate of (i) capsular saccharide of serogroup C *N meningitidis* and (ii) CRM197; (c) a conjugate of (i) capsular saccharide of serogroup Y *N. meningitidis* and (ii) tetanus toxoid; (d) a conjugate of (i) capsular saccharide of serogroup W135 *N. meningitidis* and (ii) CRM197; and (d) a conjugate of (i) capsular saccharide of serogroup X *N meningitidis* and (ii) tetanus toxoid characterized in that conjugates containing tetanus toxoid as carrier protein are found to enhance immunogenicity of conjugates containing CRM 197 as carrier protein.

composition IV comprises (a) a conjugate of (i) the capsular saccharide of serogroup A *N meningitidis* and (ii) tetanus toxoid; (b) a conjugate of (i) capsular saccharide of serogroup C *N meningitidis* and (ii) CRM197; (c) a conjugate of (i) capsular saccharide of serogroup Y *N. meningitidis* and (ii) CRM197; (d) a conjugate of (i) capsular saccharide of serogroup W135 *N. meningitidis* and (ii) CRM197; and (d) a conjugate of (i) capsular saccharide of serogroup X *N meningitidis* and (ii) tetanus toxoid.

Composition V comprises (a) a conjugate of (i) the capsular saccharide of serogroup A *N meningitidis* and (ii) CRM 197; (b) a conjugate of (i) capsular saccharide of serogroup C *N meningitidis* and (ii) CRM197; (c) a conjugate of (i) capsular saccharide of serogroup Y *N. meningitidis* and (ii) CRM197; (d) a conjugate of (i) capsular saccharide of serogroup W135 *N. meningitidis* and (ii) CRM197; and (d) a conjugate of (i) capsular saccharide of serogroup X *N meningitidis* and (ii) tetanus toxoid.

Accordingly in a first embodiment, the composition can comprise of serogroup A, C, Y, W135 and X saccharide at an amount of 0.5-10 µg, 0.5-5 µg or 0.5-2 µg per 0.5 ml dose.

Another aspect of first embodiment is that said composition can comprise of 10 µg of serogroup A saccharide, 5 µg of serogroup C saccharide, 5 µg of serogroup W135 saccharide, 5 µg of serogroup Y saccharide and 5 µg of serogroup X saccharide.

Alternatively said multivalent immunogenic composition can comprise of 5 µg of serogroup A saccharide, 5 µg of serogroup C saccharide, 5 µg of serogroup W135 saccharide, 5 µg of serogroup Y saccharide and 5 µg of serogroup X saccharide.

Accordingly in a second embodiment, said one or more *N. meningitidis* saccharide conjugates can optionally be adsorbed onto aluminium hydroxide, aluminium phosphate or a mixture of both or unadsorbed onto adjuvant.

One aspect of second embodiment is that aluminium salt adjuvant can be added at an amount of 20-300 µg, 20-200 µg, 25-150 µg of $Al^{+++}$ per 0.5 ml dose.

Another aspect of second embodiment is that aluminium salt adjuvant can be added at an amount of 25-125 µg of $Al^{+++}$ per 0.5 ml.

A third embodiment of the instant invention is that said composition can comprise of a preservative selected from thiomersal and 2-phenoxyethanol.

One aspect of third embodiment is that said can further comprise of sodium phosphate, sodium chloride or combination thereof.

A fourth embodiment of the instant invention is that said multivalent immunogenic composition can be in a buffered liquid form or in a lyophilized form.

One aspect of fourth embodiment is that said lyophilized immunogenic composition can comprise of a stabilizer combination selected from a) 2 to 5% (w/v) Trehalose, 0.25 to 0.75% sodium citrate; b) 2 to 5% (w/v) Sucrose and 0.25 to 0.75% sodium citrate; c) 2 to 5% (w/v) Sucrose, 2 to 5% (w/v) Lactose and 0.25 to 0.75% sodium citrate; and d) 2 to 5% (w/v) Trehalose, 2 to 5% (w/v) Lactose and 0.25 to 0.75% sodium citrate.

Another aspect of the fourth embodiment is that said lyophilized immunogenic composition can further comprise a buffer selected from Tris and phosphate.

Accordingly in a fifth embodiment, said polysaccharides A C W and X can be mechanically sized to have an average molecular weight between 100-600 Kda, 100-400 Kda, preferably 100-200 Kda, most preferably 100-150 Kda. Mechanical sizing methods like homogenization, microfluidization and high pressure cell disruption are preferred.

In another aspect of fifth embodiment, said polysaccharide Y can be sized to have an average molecular weight between 90-110 KDa, by a method selected from acid hydrolysis, alkaline degradation, oxidation by periodate, ozonolysis, enzymatic hydrolysis, sonication, electron beam fragmentation. Preferably, chemical sizing is by using sodium acetate at a temperature from 60 to 80° C.

In a sixth embodiment, each of the *N. meningitidis* saccharides is conjugated to the carrier protein via a hetero or homobifunctional linker with cyanylation conjugation chemistry.

In one aspect of sixth embodiment, said sized polysaccharide is activated by utilizing a cyanylation reagent selected from but not limited to 1-cyano-4-(dimethylamino)-pyridinium tetrafluoroborate ('CDAP'), p-nitrophenylcyanate and N-cyanotriethylammonium tetrafluoroborate ('CTEA'). In a preferred conjugation process, cyanylating reagent is other than CDAP and can be selected from a group of 1-cyano-4-pyrrolidinopyridinium tetrafluoroborate (CPPT), 1-cyano-imidazole (1-CI), 1-cyanobenzotriazole (1-CBT), or 2-cyanopyridazine-3(2H)one (2-CPO), or a functional derivative or modification thereof.

In another aspect of sixth embodiment, said activated polysaccharide or carrier protein, particularly polysaccharide is reacted with hydrazine, carbohydrazide, hydrazine chloride, a dihydrazide, a mixture thereof, preferably with adipic acid dihydrazide.

Hydrazide groups can be introduced into proteins through the carboxyl groups of aspartic acid and glutamic acid residues on the protein using a carbodiimide reaction, for example, by reaction with hydrazine, carbohydrazide, succinyl dihydrazide, adipic acid dihydrazide, hydrazine chloride (e.g., hydrazine dihydrochloride) or any other dihydrazides in the presence of EDC. EDC is employed as a catalyst to activate and modify the protein reactant with hydrazine or the dihydrazide. Any water-soluble carbodiimide including EDC can be used as a catalyst. EDC-catalyzed proteins generally have a tendency to polymerize and precipitate. See Schneerson et al., Infect. Immun. 1986, 52:519-528; Shafer et al., Vaccine 2000; 18(13): 1273-1281; and Inman et al., Biochemistry 1969; 8:4074-4082.

In a seventh embodiment, said multivalent meningococcal polysaccharide protein conjugate composition contains polysaccharides from A, B, C, H, I, K, L, 29E, W135, Y and Z conjugated individually to two or more different types of carrier proteins. The capsular saccharides are chosen from meningococcal serogroups A, C, W135 Y and X, such that the compositions include saccharides from 1, 2, 3, 4, or 5 of these five serogroups. Specific compositions comprise saccharides from: serogroups A & X; serogroups X & W135; serogroups X & Y; serogroups C & X; serogroups A Y & X; serogroups C, X & W135; serogroups X, Y & W135; serogroups A, C & X; serogroups Y, C & X; serogroups A, W & X; serogroups Y & W135 & C & X; serogroups Y & W135 & A & X; serogroups C & W135 & A & X; serogroups Y & C & A & X; serogroups A & C & Y & W135 & X. Compositions including at least serogroup X are preferred, and compositions including saccharides from all five serogroups are most preferred.

In an aspect of seventh embodiment, said carrier protein can be selected from a group of but not limited to CRM 197, diphtheria toxoid, tetanus toxoid, pertussis toxoid, *E. coli* LT, E: coli ST, and exotoxin A from *Pseudomonas aeruginosa*, outer membrane complex c (OMPC), porins, transferrin binding proteins, pneumolysin, pneumococcal surface protein A (PspA), pneumococcal adhesin protein (PsaA), pneumococcal surface proteins BVH-3 and BVH-11, protective antigen (PA) of *Bacillus anthracis* and detoxified edema factor (EF) and lethal factor (LF) of *Bacillus anthracis*, ovalbumin, keyhole limpet hemocyanin (KLH), human serum albumin, bovine serum albumin (BSA) and purified protein derivative of tuberculin (PPD). Preferably, combinations of carrier proteins to be utilized comprise tetanus toxoid & diphtheria toxoid, CRM197 & tetanus toxoid.

In another aspect of third embodiment, conjugation reaction utilizes linkers selected from the group consisting of adipic acid dihydrazide, ε-aminohexanoic acid, chlorohexanol dimethyl acetal, D-glucuronolactone, cystamine and p-nitrophenylethyl amine.

After conjugation, conjugates can be purified from unreacted protein and polysaccharide by any standard techniques including, inter alia, size exclusion chromatography, density gradient centrifugation, ultrafiltration, hydrophobic interaction chromatography or ammonium sulfate fractionation. See, e.g., P. W. Anderson, et. al. (1986). J. Immunol. 137: 1181-1186. See also H. J. Jennings and C. Lugowski (1981) J. Immunol. 127: 1011-1018.

In an eighth embodiment, said immunogenic composition of the instant invention can further comprise of an additional non-meningococcal polysaccharide protein conjugate, wherein said polysaccharides and oligosaccharides for use can be selected from but not limited to pneumococcal polysaccharides of serogroups 1, 2, 3, 4, 5, 6A, 6B, 7F, 8, 9N, 9V, 10A, 11A, 12F, 14, 15B, 17F, 18C, 19F, 19A, 20, 22F, 23F, and 33F; *Haemophilus influenzae* type b polysaccharide polyribosylribitol phosphate, group B streptococcal polysaccharides of serotypes III and V and *Salmonella typhi* Vi polysaccharide. Other polysaccharides of pneumococcal and group B streptococcal serotypes are also suitable for use herein, as are other T-independent polysaccharide and oligosaccharide antigens, for example, polysaccharides or oligosaccharides derived from group A *streptococcus*, Staphylococci, Enterococci, *Klebsiella pneumoniae*, *E. coli*, *Pseudomonas aeruginosa*, and *Bacillus anthracis*. While bacterial polysaccharides and oligosaccharides are particularly preferred, gram (–) bacterial lipopolysaccharides and lipooligosaccharides and their polysaccharide and oligosaccharide derivatives, and viral polysaccharides and oligosaccharides can also be employed.

Compositions of the invention may be presented and packaged in various ways. The compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

EXAMPLES

Example 1

Preparation of Meningococcal X polysaccharide a) Fermentation and Purification of Meningococcal X Polysaccharide Meningococcal X polysaccharides are obtained from *N. meningitidis* strains (8210 & 9601) by utilizing a suitable fermentation medium in a continuous fed-batch fermentation mode under optimal fermentor conditions. Further Meningococcal X capsular polysaccharides are typically prepared by a process comprising the steps of CTAB based precipitation, Ethanol (96%) treatment followed by depth filtration, carbon filtration, $CaCl_2$ precipitation, Ethanol (96%) treatment and ultrafiltration.

b) Sizing of Meningococcal X Polysaccharide

Purified Meningococcal X polysaccharides were subjected to 1-2 passes of mechanical sizing (Constant systems cell disruptor) in WFI at a pressure of about 30-40 kpsi.

Example 2

Conjugation of Meningococcal X Polysaccharide to Carrier Protein a) Meningococcal X Polysaccharide of Varying Average Molecular Weight Conjugated to Hydrazine Derivatized Tetanus Toxoid (TT)

Firstly homogenized Polysaccharide of X (Strain 9601), Average molecular weight 215 kD on SEC HPLC, (30 mg/ml) 45 mg was activated with 90 mg CDAP (dissolved 100 mg/ml in acetonitrile), pH of mixture was adjusted to 9.5 with 1M NaOH. Then after 3 min hydrazine activated TT (30 mg/ml in 1M NaCl) 67.5 was added to the reaction. The reaction was monitored on HPLC and continued upto 18 hrs. After 18 hrs reaction was quenched by addition of glycine and crude conjugate was purified by diafiltration 300 kD TFF membrane in Tris 10 mM pH 7.2. Shodex columns SB-804 HQ and SB-805 HQ were used sequentially with PBS as mobile phase at 1 ml/min flow rate. Polysaccharide concentration and protein concentration were determined by phosphorous assay and modified Lowry assay respectively.

Secondly Polysaccharide of X (Strain 8210), average molecular weight 326 kD on SEC HPLC, (24 mg/ml in 2M NaCl) 60 mg was activated with 150 mg CPPT (dissolved 114 mg/ml in acetonitrile) and pH of mixture was adjusted to 9.5 with 2.5M NaOH. Then after 3 min ADH activated TT (37 mg/ml in 2M NaCl) 37.5 mg was added to the reaction and the reaction was monitored on HPLC and continued upto 5 hrs. After 5 hrs reaction was quenched by addition of glycine and crude conjugate was purified by diafiltration with 500 kD TFF membrane in 10 mM PBS followed by Tris 10 mM pH 7.2.

Further Polysaccharide of X (Strain 8210), having average molecular weight 120 kD on SEC HPLC, (20 mg/ml in 1M NaCl) 200 mg was activated with 400 mg CPIP (dissolved 114 mg/ml in acetonitrile), and pH of mixture was adjusted to 9.5 with 1M NaOH. Then after 3 min ADH activated TT (30 mg/ml) 150 mg was added to the reaction. The reaction was monitored on HPLC and continued upto 4 hrs. After 4 hrs reaction was quenched by addition of glycine and crude conjugate was purified by diafiltration with 300 kD TFF membrane in 10 mM PBS followed by Tris 10 mM pH 7.2.

b) Meningococcal X Polysaccharide of Varying Average Molecular Weight Activated with ADH and Conjugated to Purified Non-Activated Tetanus Toxoid (TT)

Firstly Polysaccharide of X (Strain 8210) having average molecular weight 510 kD on SEC HPLC (27 mg/ml in 2M NaCl) 200 mg was activated with 400 mg CPPT (dissolved 114 mg/ml in acetonitrile) and pH of mixture was adjusted to 9.5 with 2.5M NaOH. Then after 3 min, ADH 1.5 g (100 mg/ml in carbonate buffer) was added and reaction was continued upto 4 hrs. After 4 hrs glycine was added and reaction mixture was diafiltered on 8 kD TFF membrane. Further ADH-Men X polysaccharide was concentrated. To 44 mg of this (7.5 mg/ml), purified TT (37.5 mg/ml in 0.9% NaCl) and MES pH 6.0 buffer were added so that final buffer strength of MES was 100 mM, followed by addition of 37.5 mg EDAC (dissolved in 100 mM MES, pH 6.0). The reaction was continued for 4 hrs and monitored on HPLC. Unbound polysaccharide was removed by Gel filtration Chromatography using Toyopearl HW65 resin on Akta Chromatography System. (GE Amersham). The fractions were collected and pooled based on peak profile and saccharide-protein ratio.

Secondly, Polysaccharide of X (Strain 8210) having average molecular weight 250 kD on SEC HPLC was concentrated to 18 mg/ml in 2M NaCl. A quantity of 200 mg was activated with 296 mg CPPT (dissolved 114 mg/ml in acetonitrile) and pH of mixture was adjusted to 9.5 with 2.5M NaOH. Then after 3 min ADH 1.12 g (100 mg/ml in carbonate buffer) was added and reaction was continued upto 4 hrs. After 4 hrs glycine was added and reaction mixture was diafiltered on 8 kD TFF membrane. ADH-Men X polysaccharide was then concentrated. Further to 200 mg of this (7.5 mg/ml), purified TT (36.7 mg/ml in 0.9% NaCl) and MES pH 6.0 buffer were added so that final buffer strength of MES was 100 mM, followed by addition of 200 mg EDAC (dissolved in 100 mM MES, pH 6.0). The reaction was continued for 4 hrs and monitored on HPLC. The crude conjugate was purified by diafiltration 500 kD TFF membrane in 10 mM PBS followed by Tris 10 mM pH 7.2.

TABLE 1

Meningococcal X polysaccharide-protein Conjugation

| Avg Mw of Meningococcal X polysaccharide (KDa) | ADH activation | Saccharide/Protein ratio | Polysaccharide Titer (mg/ml) | Protein Titer (mg/ml) |
| --- | --- | --- | --- | --- |
| 215 | TT (ADH activated) | 0.23 | 0.211 | 0.921 |
| 326 | TT (ADH activated) | 0.57 | 0.25 | 0.435 |
| 120 | Meningococcal X polysaccharide (ADH activated); TT non-activated | 0.59 | 0.20 | 0.34 |
| 510 | Meningococcal X polysaccharide (ADH activated); TT non-activated | 0.53 | 0.180 | 0.34 |
| 250 | Meningococcal X polysaccharide (ADH activated); TT non-activated | 0.43 | 0.130 | 0.30 |

Above data indicates that final conjugate yield of about 20 to 30% can be obtained by utilizing i) Meningococcal X polysaccharide of Avg Mw of about 100 to 200 kDa, ii) ADH activated Meningococcal X polysaccharide iii) non-activated TT iv) saccharide:protein ratio between 0.5 to 2 during conjugation reaction v) CPPT as cyanylation reagent and vi) conjugation reaction incubation at 2 to 8° C. vi) saccharide:protein ratio between 0.2 to 0.6 in final conjugate.

Example 3

Conjugation of Meningococcal A, C, Y, W135 Polysaccharide to Carrier Protein CRM197

Purified Meningococcal polysaccharides A C Y W135 having average Mw between 100 to 200 were conjugated to CRM197 in a saccharide:protein ratio of less than 1 by utilizing a suitable cyanylation reagent (CDAP or CPPT). The conjugates were further purified by diafiltration on 300 kD TFF with 50 volumes of 10 mM PBS and 50 volume of 10 mM Tris.

Example 4

Lyophilization & Formulation of Men A C Y W135 & X Conjugate Containing Two Different Carrier Proteins Lyophilized formulations containing *N. meningitidis* conjugates, sodium citrate and Tris buffer in various combinations with trehalose, sucrose and lactose were prepared wherein free polysaccharide content was within limits and moisture content was less than 2%. Said stabilizer combination was selected from a) 2 to 5% (w/v) Trehalose, 0.25 to 0.75% sodium citrate; b) 2 to 5% (w/v) Sucrose and 0.25 to 0.75% sodium citrate; c) 2 to 5% (w/v) Sucrose, 2 to 5% (w/v) Lactose and 0.25 to 0.75% sodium citrate; and d) 2 to 5% (w/v) Trehalose, 2 to 5% (w/v) Lactose and 0.25 to 0.75% sodium citrate.

TABLE 2

Liquid formulation containing Monovalent Men X-tetanus toxoid conjugate

| Formulation Code | Strain | Composition | Amount per 0.5 ml |
|---|---|---|---|
| IRCXLT1 | 9601 | Men X-TT conjugate + Saline + Thiomersal | 0.5 μg |
| IRCXLTA1 | 9601 | Men X-TT conjugate + Saline + Thiomersal + AlPO4 | 0.5 μg with 125 μg $Al^{+++}$ |
| IRCXNT1 | 9601 | Men X-TT conjugate + Saline + Thiomersal | 1 μ |
| IRCXNAT1 | 9601 | Men X-TT conjugate + Saline + Thiomersal + AlPO4 | 1 μg with 125 μg $Al^{+++}$ |
| IRCX2LT1 | 8210 | Men X-TT conjugate + Saline + Thiomersal | 0.5 μg |
| IRCX2LAT1 | 8210 | Men X-TT conjugate + Saline + Thiomersal | 0.5 μg with 125 μg $Al^{+++}$ |
| IRCX2NT1 | 8210 | Men X-TT conjugate + Saline + Thiomersal | 1 μg |
| IRCX2NATA1 | 8210 | Men X-TT conjugate + Saline + Thiomersal | 1 μg with 125 μg $Al^{+++}$ |

TABLE 3

Multivalent Liquid formulation containing Men X—tetanus toxoid conjugate

Composition amount per 0.5 ml (μ)

| Formulation Code | Strain | A-CRM 197 | C-CRM 197 | Y-CRM 197 | W-CRM 197 | X-TT | Excipients |
|---|---|---|---|---|---|---|---|
| IRCPT1 | 9601 | 1 | 1 | 1 | 1 | 1 | Sodium Chloride and Thiomersal |
| IRCPTA1 | 9601 | 1 | 1 | 1 | 1 | 1 | Sodium Chloride Thiomersal + 125 μg $Al^{+++}$ |
| IRCP2T1 | 8210 | 1 | 1 | 1 | 1 | 1 | Sodium Chloride and Thiomersal |
| IRCP2TA1 | 8210 | 1 | 1 | 1 | 1 | 1 | Sodium Chloride Thiomersal + 125 μg $Al^{+++}$ |

TABLE 4

Multivalent Liquid formulation containing Men X—TT conjugate (Strain 8210)

Composition amount per 0.5 ml (μ)

| Formulation Code | A-CRM 197 | C-CRM 197 | Y-CRM 197 | W-CRM 197 | X-TT | Excipients |
|---|---|---|---|---|---|---|
| IRCP4T1 | 1 | 1 | 1 | 1 | 1 | Sodium Chloride and Thiomersal |
| IRCP4TA1 | 1 | 1 | 1 | 1 | 1 | Sodium Chloride Thiomersal + 25 μg $Al^{+++}$ |

TABLE 5

Multivalent Liquid formulation containing Men X—TT conjugate (Strain 8210)

Composition amount per 0.5 ml (μ)

| Formulation Code | A-CRM 197 | C-CRM 197 | Y-TT | W-CRM 197 | X-TT | Excipients |
|---|---|---|---|---|---|---|
| IRCP5T1 | 1 | 1 | 1 | 1 | 1 | Sodium Chloride and Thiomersal |
| IRCP5TA1 | 1 | 1 | 1 | 1 | 1 | Sodium Chloride Thiomersal + 25 μg $Al^{+++}$ |

TABLE 6

Lyophilized multivalent formulation containing Men X—TT conjugate (Strain 8210)

Composition amount per Vial

| Formulation Code | A-CRM 197 | C-CRM 197 | Y-TT | W-CRM 197 | X-TT | Excipients Quantity in a vial |
|---|---|---|---|---|---|---|
| IRCLPS3Sc | 25 | 25 | 25 | 25 | 25 | Tris 0.6 mg, Sucrose 15 mg, Sodium citrate 2.5 mg |
| IRCLPT3Sc | 25 | 25 | 25 | 25 | 25 | Tris, Trehalose 15 mg, Sodium citrate 2.5 mg |
| IRCLPS3L2Sc | 25 | 25 | 25 | 25 | 25 | Tris, Sucrose 15 mg, Lactose 10 mg, Sodium citrate 2.5 mg |

Example 5

Biological Activity of Meningococcal Monovalent and Multivalent Conjugate Composition Containing Men X Saccharide Conjugate Each formulation was immunized into six female Swiss Albino Mice of 16-20 g body weight. Mice were immunized subcutaneously on Day 0, 14 and 28. Each mouse was bled after 1 & 2 week post second immunization (Day 21 and Day 35).

Titration of antibody was done by bead based assay and SBA. Pre-immunization serum samples from all six mice were mixed to prepare a single pool serum for each formulation from study 4 onwards and also postimmunization serum sample from six mice all belonging to Swiss Albino strain for each formulation were mixed to prepare pool 1, 2 & 3 using serum from Mouse1+2, 3+4 and 5+6, respectively. Each of the pools was analyzed for total IgG titers (Multiplexed bead based assay) and functional antibody titers (SBA).

TABLE 7

| Formulation Code | Ig G | | | SBA | | |
|---|---|---|---|---|---|---|
| | Day 21 | Day 28 | Day 35 | Day 21 | Day 28 | Day 35 |
| IRCXLT1 | 504 | 800 | 12800 | 8 | 20 | 128 |
| IRCXLTA1 | 12800 | 32254 | 51200 | 256 | 323 | 323 |
| IRCXNT1 | 2540 | 2540 | 8063 | 81 | 51 | 406 |
| IRCXNAT1 | 6400 | 12800 | 32254 | 203 | 323 | 406 |

TABLE 8

| Formulation Code | Ig G | | SBA | |
|---|---|---|---|---|
| | Day 28 | Day 35 | Day 28 | Day 35 |
| IRCX2LT1 | 79 | 3200 | 2 | 20 |
| IRCX2LAT1 | 4032 | 40637 | 20 | 128 |
| IRCX2NT1 | 1270 | 51200 | 5 | 256 |
| IRCX2NATA1 | 16127 | 51200 | 5 | 256 |

TABLE 9

| | Men A | | | | | | Men C | | | | | |
|---|---|---|---|---|---|---|---|---|---|---|---|---|
| | Ig G | | | SBA | | | Ig G | | | SBA | | |
| Formulation Code | Day 21 | Day 28 | Day 35 | Day 21 | Day 28 | Day 35 | Day 21 | Day 28 | Day 35 | Day 21 | Day 28 | Day 35 |
| IRCPT1 | 200 | 200 | 2016 | 2 | 2 | 13 | 635 | 800 | 8063 | 2 | 2 | 16 |
| IRCPTA1 | 20319 | 25600 | 32254 | 13 | 13 | 51 | 16127 | 16127 | 20319 | 25 | 32 | 102 |

TABLE 10

| | Men W135 | | | | | | Men Y | | | | | |
|---|---|---|---|---|---|---|---|---|---|---|---|---|
| | Ig G | | | SBA | | | Ig G | | | SBA | | |
| Formulation Code | Day 21 | Day 28 | Day 35 | Day 21 | Day 28 | Day 35 | Day 21 | Day 28 | Day 35 | Day 21 | Day 28 | Day 35 |
| IRCPT1 | 3200 | 3200 | 16127 | 20 | 20 | 81 | 252 | 200 | 1270 | 2 | 16 | 5 |
| IRCPTA1 | 1600 | 2016 | 12800 | 40 | 3 | 25 | 504 | 635 | 1270 | 10 | 6 | 8 |

TABLE 11

| | Men X | | | | | |
|---|---|---|---|---|---|---|
| | Ig G | | | SBA | | |
| Formulation Code | Day 21 | Day 28 | Day 35 | Day 21 | Day 28 | Day 35 |
| IRCPT1 | 1600 | 2016 | 32254 | 64 | 40 | 256 |
| IRCPTA1 | 5080 | 10159 | 51200 | 81 | 102 | 406 |

TABLE 12

| | Men A | | | | Men C | | | | Men W | | | |
|---|---|---|---|---|---|---|---|---|---|---|---|---|
| | Ig G | | SBA | | Ig G | | SBA | | Ig G | | SBA | |
| Formulation Code | Day 28 | Day 35 | Day 28 | Day 35 | Day 28 | Day 35 | Day 28 | Day 35 | Day 28 | Day 35 | Day 28 | Day 35 |
| IRCP2T1 | 79 | 252 | 2 | 5 | 400 | 6400 | 3 | 20 | 800 | 10159 | 6 | 81 |
| IRCP2TA1 | 3200 | 10159 | 5 | 16 | 3200 | 25600 | 10 | 25 | 3200 | 32254 | 2 | 20 |

TABLE 13

| | Men Y | | | | Men X | | | |
|---|---|---|---|---|---|---|---|---|
| | Ig G | | SBA | | Ig G | | SBA | |
| Formulation Code | Day 28 | Day 35 | Day 28 | Day 35 | Day 28 | Day 35 | Day 28 | Day 35 |
| IRCP2T1 | 504 | 5080 | 25 | 64 | 2540 | 20319 | 16 | 81 |
| IRCP2TA1 | 1600 | 10159 | 3 | 81 | 6400 | 32254 | 40 | 102 |

TABLE 14

| Formulation Code | Men A SBA Day 35 | Men C SBA Day 35 | Men W135 SBA Day 35 | Men Y SBA Day 35 | Men X SBA Day 35 |
|---|---|---|---|---|---|
| IRCP4T1 | 13 | 10 | 20 | 8 | 512 |
| IRCP4TA1 | 16 | 25 | 6 | 5 | 512 |
| IRCP5T1 | 13 | 25 | 10 | 256 | 406 |
| IRCP5TA1 | 203 | 203 | 102 | 1625 | 512 |

TABLE 15

| | Men A | | | | Men C | | | | Men W135 | | | |
|---|---|---|---|---|---|---|---|---|---|---|---|---|
| | Ig G | | SBA | | Ig G | | SBA | | Ig G | | SBA | |
| Formulation Code | Day 28 | Day 35 | Day 28 | Day 35 | Day 28 | Day 35 | Day 28 | Day 35 | Day 28 | Day 35 | Day 28 | Day 35 |
| IRCLPS3Sc | 635 | 4032 | 2 | 5 | 3200 | 6400 | 2 | 25 | 3200 | 10159 | 6 | 40 |
| IRCLPS3DSc+AlPO4 | 1600 | 6400 | 3 | 25 | 4032 | 25600 | 20 | 323 | 4032 | 12800 | 13 | 64 |
| IRCLPT3Sc | 200 | 1270 | 2 | 6 | 317 | 2540 | 4 | 25 | 2016 | 4032 | 10 | 64 |
| IRCLPT3Sc+AlPO4 | 1600 | 6400 | 5 | 51 | 3200 | 10159 | 25 | 102 | 2540 | 16127 | 20 | 102 |
| IRCLPS3L2Sc | 317 | 1270 | 2 | 2 | 800 | 1600 | 5 | 13 | 1600 | 4032 | 64 | 203 |
| IRCLPS3L2Sc+AlPO4 | 635 | 1270 | 5 | 8 | 5080 | 10159 | 13 | 64 | 3200 | 8063 | 8 | 25 |

TABLE 16

| | Men Y | | | | Men X | | | |
|---|---|---|---|---|---|---|---|---|
| | Ig G | | SBA | | Ig G | | SBA | |
| Formulation Code | Day 28 | Day 35 | Day 28 | Day 35 | Day 28 | Day 35 | Day 28 | Day 35 |
| IRCLPS3Sc | 800 | 1008 | 8 | 5 | 1008 | 16127 | 32 | 323 |
| IRCLPS3DSc+AlPO4 | 2540 | 16127 | 25 | 323 | 3200 | 51200 | 40 | 406 |
| IRCLPT3Sc | 504 | 4032 | 6 | 32 | 252 | 12800 | 16 | 323 |
| IRCLPT3Sc+AlPO4 | 504 | 4032 | 4 | 256 | 1270 | 16127 | 8 | 256 |
| IRCLPS3L2Sc | 504 | 2016 | 10 | 162 | 317 | 12800 | 10 | 406 |
| IRCLPS3L2Sc+AlPO4 | 635 | 1600 | 5 | 8 | 400 | 2016 | 64 | 102 |

Above mice immunogenicity data indicates that liquid and lyophilized compositions of monovalent X-tetanus toxoid conjugate and multivalent conjugates containing X-tetanus toxoid conjugate are found to be immunogenic. Further monovalent liquid composition containing 1 µg of X-tetanus toxoid conjugate, sodium chloride, thiomersal and 125 µg $Al^{+++}$ gives optimal immunogenic response. Also liquid multivalent composition of 0.5 ml containing A-CRM197, C-CRM197, Y-tetanus toxoid, W-CRM197 and X-tetanus toxoid conjugates with 1 µg each of all 5 saccharides, sodium chloride, thiomersal and 25 µg $Al^{+++}$ gives optimal immunogenic response. Thus in this pentavalent conjugate composition, conjugates containing tetanus toxoid as carrier protein are found to enhance immunogenicity of conjugates containing CRM 197 as carrier protein.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. An immunogenic composition comprising
   (a) a conjugate of (i) the capsular saccharide of serogroup A *N. meningitidis* and (ii) tetanus toxoid;
   (b) a conjugate of (i) capsular saccharide of serogroup C *N. meningitidis* and (ii) CRM197;
   (c) a conjugate of (i) capsular saccharide of serogroup Y *N. meningitidis* and (ii) CRM197;
   (d) a conjugate of (i) capsular saccharide of serogroup W135 *N. meningitidis* and (ii) CRM197; and
   (e) a conjugate of (i) capsular saccharide of serogroup X *N. meningitidis* and (ii) tetanus toxoid wherein the *N. meningitidis* X polysaccharide-protein conjugate is derived from *N. meningitidis* X strain 8210, 9601, 9592, 9554 or 2526.

2. The immunogenic composition of claim 1, wherein the serogroup X *N. meningitidis* is *N. meningitidis* X strain 8210 or 9601.

3. The immunogenic composition of claim 1, wherein each capsular saccharide has an average size of between 100 and 600 KDa, or between 100 and 300 KDa, or between 100 and 200 KDa.

4. The immunogenic composition of claim 1, wherein at least 3 *N. meningitidis* saccharides from serogroups A, C, W135 and X post-sizing have an average size of between 100 and 150 KDa.

5. The immunogenic composition of claim 3, wherein the sizing is made by using a high pressure cell disruption system.

6. The immunogenic composition of claim 1, wherein a *N. meningitidis* saccharide from serogroup Y post-chemical sizing has an average size of between 90 and 110 KDa.

7. The immunogenic composition of claim 6, wherein the chemical sizing is made by using sodium acetate at a temperature from 60 to 80° C.

8. The immunogenic composition of claim 1, wherein each of the *N. meningitidis* saccharides is conjugated to the carrier protein via a hetero or homo-bifunctional linker with cyanylation conjugation chemistry.

9. The immunogenic composition of claim 8, wherein the linker is ADH.

10. The immunogenic composition of claim 8, wherein a cyanylation reagent used in the cyanylation conjugation chemistry is 1-cyano-4-pyrrolidinopyridinium tetrafluoroborate (CPPT), 1-cyano-imidazole (1-CI), 1-cyanobenzotriazole (1-CBT), or 2-cyanopyridazine-3(2H)one (2-CPO).

11. The immunogenic composition of claim 8, wherein the *N. meningitidis* X saccharide-tetanus toxoid conjugates are prepared by a conjugation reaction comprising:
   i) sizing of the polysaccharide;
   ii) a CPPT based activation of a sized polysaccharide having average molecular weight between 100-150 Kda, at a pH between 9 to 9.5;
   iii) an ADH addition after a duration of about 2 to 3 minutes followed by an incubation period of 4-20 hrs;
   iv) diafiltration to remove unreacted ADH; and
   v) reacting ADH activated polysaccharide with purified non-activated carrier protein in a ratio between 0.75-1.5 in presence of MES buffer and EDAC followed by an incubation period of 3-4 hrs, wherein the conjugation reaction is carried at a temperature between 2-8° C. and the ratio of saccharide to protein in final conjugate is between 0.2 to 0.6.

12. The immunogenic composition of claim 8, wherein the *N. meningitidis* X saccharide-tetanus toxoid conjugates are prepared by a conjugation reaction comprising:
   i) sizing of the polysaccharide;
   ii) a CPPT based activation of sized polysaccharide having average molecular weight between 100-150 Kda, at a pH between 9 to 9.5;
   iii) an addition of ADH activated carrier protein in a saccharide to protein ratio of between 0.5-2 after 2-3 minutes followed by incubation period of 2 to 20 hrs, wherein the conjugation reaction is carried at 22° C. to about 25° C. and the ratio of saccharide to protein in final conjugate is between 0.2 to 0.6.

13. An immunogenic composition comprising
   a *N. meningitidis* X polysaccharide-protein conjugate derived from *N. meningitidis* X strain 8210, 9601, 9592, 9554 or 2526; and
   at least one additional saccharide conjugate(s) from a *N. meningitidis* capsular saccharide derived from serogroups A, B, C, W135 or Y.

14. The immunogenic composition of claim 13, wherein the *N. meningitidis* X strain is 8210 or 9601.

15. The immunogenic composition of claim 13, wherein the immunogenic composition comprises a capsular polysaccharide of *N. meningitidis* serogroups A, C, W-135, Y and X by utilizing at least 2 different carrier proteins for conjugating all 5 polysaccharides.

16. The immunogenic composition of claim 13, wherein each *N. meningitidis* saccharide(s) are conjugated to a carrier protein selected from the group consisting of TT, DT, CRM197, fragment C of TT, protein D and pneumolysin.

17. The immunogenic composition of claim 15, wherein the composition comprises:
   (a) a conjugate of (i) the capsular saccharide of serogroup A *N. meningitidis* and (ii) tetanus toxoid;
   (b) a conjugate of (i) capsular saccharide of serogroup C *N. meningitidis* and (ii) CRM197;
   (c) a conjugate of (i) capsular saccharide of serogroup Y *N. meningitidis* and (ii) tetanus toxoid;
   (d) a conjugate of (i) capsular saccharide of serogroup W135 *N. meningitidis* and (ii) CRM197; and
   (e) a conjugate of (i) capsular saccharide of serogroup X *N. meningitidis* and (ii) CRM197.

18. The immunogenic composition of claim 15, wherein each capsular saccharide has an average size of between 100 and 600 KDa, or between 100 and 300 KDa, or between 100 and 200 KDa.

19. The immunogenic composition of claim 15, wherein at least 3 *N. meningitidis* saccharides from serogroups A, C, W135 and X post-sizing have an average size of between 100 and 150 KDa.

20. The immunogenic composition of claim 18, wherein the sizing is made by using a high pressure cell disruption system.

21. The immunogenic composition of claim 15, wherein a *N. meningitidis* saccharide from serogroup Y post-chemical sizing has an average size of between 90 and 110 KDa.

22. The immunogenic composition of claim 21, wherein the chemical sizing is made by using sodium acetate at a temperature from 60 to 80° C.

23. The immunogenic composition of claim 15, wherein each of the *N. meningitidis* saccharides is conjugated to the carrier protein via a hetero or homo-bifunctional linker with cyanylation conjugation chemistry.

24. The immunogenic composition of claim 23, wherein the linker is ADH.

25. The immunogenic composition of claim 23, wherein a cyanylation reagent used in the cyanylation conjugation chemistry is 1-cyano-4-pyrrolidinopyridinium tetrafluoroborate (CPPT), 1-cyano-imidazole (1-CT), 1-cyanobenzotriazole (1-CBT), or 2-cyanopyridazine-3(2H)one (2-CPO).

26. The immunogenic composition of claim 23, wherein the *N. meningitidis* X saccharide-tetanus toxoid conjugates are prepared by a conjugation reaction comprising:
   i) sizing of the polysaccharide;
   ii) a CPPT based activation of a sized polysaccharide having average molecular weight between 100-150 Kda, at a pH between 9 to 9.5;
   iii) an ADH addition after a duration of about 2 to 3 minutes followed by an incubation period of 4-20 hrs;
   iv) diafiltration to remove unreacted ADH; and
   v) reacting ADH activated polysaccharide with purified non-activated carrier protein in a ratio between 0.75-1.5 in presence of MES buffer and EDAC followed by an incubation period of 3-4 hrs, wherein the conjugation reaction is carried at a temperature between 2-8° C. and the ratio of saccharide to protein in final conjugate is between 0.2 to 0.6.

27. The immunogenic composition of claim 23, wherein the *N. meningitidis* X saccharide-tetanus toxoid conjugates are prepared by a conjugation reaction comprising:
   i) sizing of the polysaccharide;
   ii) a CPPT based activation of sized polysaccharide having average molecular weight between 100-150 Kda, at a pH between 9 to 9.5; and
   iii) an addition of ADH activated carrier protein in a saccharide to protein ratio of between 0.5-2 after 2-3 minutes followed by incubation period of 2 to 20 hrs, wherein the conjugation reaction is carried at 22° C. to about 25° C. and the ratio of saccharide to protein in final conjugate is between 0.2 to 0.6.

* * * * *